United States Patent [19]

Kleiner

[11] Patent Number: 5,734,072
[45] Date of Patent: Mar. 31, 1998

[54] PROCESS FOR PREPARING MONOALKYL PHOSPHONITES

[75] Inventor: Hans-Jerg Kleiner, Kronberg, Germany

[73] Assignee: Hoechst Aktiengesellschaft, Frankfort, Germany

[21] Appl. No.: 794,439

[22] Filed: Feb. 5, 1997

[30] Foreign Application Priority Data

Feb. 6, 1996 [DE] Germany .................. 196 04 195.3

[51] Int. Cl.⁶ .................................................. C07F 9/48
[52] U.S. Cl. .................................................. 558/96
[58] Field of Search .................................... 558/96

[56] References Cited

U.S. PATENT DOCUMENTS

| | | |
|---|---|---|
| 2,903,475 | 9/1959 | Harowitz ................. 558/96 |
| 5,013,863 | 5/1991 | Baylis et al. . |
| 5,051,524 | 9/1991 | Baylis et al. . |
| 5,190,934 | 3/1993 | Mickel et al. . |

FOREIGN PATENT DOCUMENTS

| | | |
|---|---|---|
| 0319479 | 6/1989 | European Pat. Off. . |
| 0319482 | 5/1994 | European Pat. Off. . |
| 0402312 | 1/1995 | European Pat. Off. . |
| 853982 | 11/1960 | United Kingdom . |

OTHER PUBLICATIONS

Gladshtein, B.M. et al. Synthesis of Alkylphosphonous Esters. J. Gen. Chem. USSR, 39, 1913–1915 (1969).
Gladshtein, B.M., et al, *Zh. Obsh. Khim* 39:1951–1953 (1969).

B. M. Gladshtein et al, Journal of General Chemistry USSR, 39, (No. 9), 1969, New York, pp. 1913–1915, Synthesis of Alkylphosphonous esters.

*Primary Examiner*—Michael G. Ambrose
*Attorney, Agent, or Firm*—Connolly & Hutz

[57] ABSTRACT

The invention relates to a process for preparing monoalkyl phosphonites of the formula I $$R^1-\underset{\underset{H}{|}}{\overset{\overset{O}{\|}}{P}}-OR^2 \quad (I)$$

where $R^1$ is $(C_1-C_{16})$-alkyl, cyclohexyl, cyclopentyl, or phenyl, each of which can also be substituted by halogen, $(C_1-C_6)$-alkyl, $(C_1-C_6)$-alkoxy or dialkylamino groups and $R^2$ is $(C_1-C_8)$-alkyl, which comprises reacting dichlorophosphines of the formula (II)

$$R^1-PCl_2 \quad (II)$$

where $R^1$ has the meaning given above, with alcohols of the formula (III)

$$R^2OH \quad (III)$$

where $R^2$ has the meaning given above, the molar ratio of dichlorophosphine/alcohol being 1:3 to 1:20, and then, as soon as the content of ionic chlorine in the reaction mixture is 50–75% of the theoretical total chlorine content of the reaction mixture, reacting the mixture with ammonia.

20 Claims, No Drawings

PROCESS FOR PREPARING MONOALKYL PHOSPHONITES

The invention relates to a process for preparing monoalkyl phosphonites.

Monoalkyl phosphonites are of great interest as intermediates for preparing flame retardants, herbicides, biocidal auxiliaries and metal extraction compositions. In particular, they are also of importance for preparing medicaments, for example for preparing antidepressive and/or antiepileptic medicaments (EP-A 319 479, EP-A 402 312 and EP-B 319 482).

Short-chain monoalkyl phosphonites are generally prepared by reacting dichlorophosphines with alcohols, in the presence or absence of amines or ammonia in accordance with the following scheme:

$$RPCl_2 + 2\,ROH \longrightarrow \underset{H}{\underset{|}{RP}}\!\!-\!OR + RCl + HCl$$
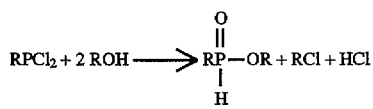

(B. M. Gladshtein et al., Zh. Obsh. Khim 39, 1951 (1969)). Preference is given to the use of ammonia as base for this. The reaction proceeds at −60° to −40° C. with addition of 2 mol of alcohol to 1 mol of dichlorophosphine in dichloromethane as solvent. The yields are about 70% of theory. The necessity to employ very low temperatures is, in particular, unsatisfactory in this process. The yields are likewise not completely satisfactory.

There was therefore the need to improve this ammonia process in such a manner that the desired products are formed in high yield and high purity without great use of technical resources.

This object is achieved by a process for preparing monoalkyl phosphonites of the formula I $$R^1\!\!-\!\!\underset{H}{\underset{|}{\overset{\overset{O}{\|}}{P}}}\!\!-\!OR^2 \qquad (I)$$
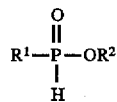

where $R^1$ is $(C_1-C_{16})$-alkyl, cyclohexyl, cyclopentyl, phenyl, each of which can also be substituted by halogen, $(C_1-C_6)$-alkyl, $(C_1-C_6)$-alkoxy or dialkylamino groups and $R^2$ is $(C_1-C_8)$-alkyl, which comprises reacting dichlorophosphines of the formula (II)

$$R^1\!\!-\!\!PCl_2 \qquad (II)$$

where $R^1$ has the meaning given above, with alcohols of the formula (III)

$$R^2OH \qquad (III)$$

where $R^2$ has the meaning given above, the molar ratio of dichlorophosphine/alcohol being 1:3 to 1:20, and then, as soon as the content of ionic chlorine in the reaction mixture is 50–75% of the theoretical total chlorine content of the reaction mixture, reacting the mixture with ammonia.

The reaction is of importance for compounds where $R^2$ is $(C_1-C_6)$-alkyl, in particular $(C_1-C_4)$-alkyl.

The reaction is of particular interest for the reaction of dichloromethylphosphine, dichloroethylphosphine, dichloropropylphosphine, dichlorobutylphosphine, dichlorocyclohexylphosphine, dichlorophenylphosphine, dichloro-4-methoxyphenylphosphine and dichloro-4-dimethylaminophenylphosphine.

Suitable alcohols are e.g. methanol, ethanol, isopropanol or n-butanol. Preference is given in particular to ethanol. The alcohols must be as free as possible from water. They must be used in excess. This excess is in a ratio of dichlorophosphine:alcohol of 1:3 to 1:20, in particular 1:4.5 to 1:15. In addition, inert solvents such as toluene or chlorobenzene can be used.

The process is advantageously carried out in such a manner that the dichlorophosphine is added to the alcohol, if appropriate mixed with the solvent, at −20° to +30° C., preferably −10° to +10° C., under a nitrogen atmosphere. The mixture is then further stirred until 50–75%, preferably 50–65%, of the theoretical total chlorine content of the reaction mixture are found. This total chlorine content is calculated from the chlorine content of the reaction mixture as must result from the admixture of the dichlorophosphine. The further stirring period can be shortened by heating the reaction mixture, but in general temperatures of 50°–60° C. must not be exceeded. The mixture is then reacted with ammonia, this expediently being used in an excess of 5 to 20 mol %, in order to ensure that the reaction product remains in the alkaline region. After the reaction is completed, the mixture is expediently further stirred at room temperature, then filtered off by suction from ammonium chloride formed. The addition of inert solvents may be expedient here, in particular in the preparation of the methyl esters, in order to make the precipitation of the ammonium chloride quantitative. The filtrate is worked up by distillation in a customary manner. The process can also be made continuous. For certain fields of application, the monoesters of phosphonous acid prepared according to the process can, even as crude products, be so pure that purification by distillation is not necessary.

EXAMPLE 1

200 g (1.71 mol) of dichloromethylphosphine are added dropwise to 500 g (6.76 mol) of isobutanol in the course of one hour and 40 minutes under a nitrogen atmosphere, with stirring, at 5°–10° C. The mixture is then heated at approximately 50° C. for 55 minutes, then cooled to room temperature. The reaction batch then contains 8.9% of ionic chlorine. Ammonia is then passed in for one hour with cooling at 20°–25° C., then the mixture is further stirred for 20 minutes and filtered off with suction, and the precipitate is washed with 80 g of isobutanol. The filtrate is freed from the low boilers in vacuo and then distilled at 2.5–3 mbar at 100° C. using a thin-film evaporator. 215 g of monoisobutyl methanephosphonite are obtained. This corresponds to a yield of 92.5% of theory.

EXAMPLE 2

200 g (1.71 mol) of dichloromethylphosphine are added dropwise to 400 g (12.5 mol) of methanol in the course of two hours under a nitrogen atmosphere, with stirring, at 0° C. The mixture is then further stirred for 3 hours at 5°–8° C. The reaction batch then contains approximately 11.6% of ionic chlorine. Ammonia is then passed in at 0° C. until the reaction batch gives a neutral reaction. The mixture is then heated to 30° C., outgassing methyl chloride. The mixture is then cooled, filtered off with suction and the precipitate washed with 80 g of methanol. The filtrate is freed from low boilers and the residue is distilled. 128 g of monomethyl methanephosphonite are obtained at 30 mbar and an over-

EXAMPLE 3

200 g (1.71 mol) of dichloromethylphosphine are added dropwise to 500 g (8.34 mol) of isopropanol at 5°–10° C. in the course of two hours under a nitrogen atmosphere with stirring. The mixture is then heated to 30°–35° C. until the ionic chlorine figure is approximately 9.6%. Ammonia gas is then passed in at 15°–20° C. until the reaction batch gives a neutral reaction. The mixture is then filtered off with suction, the precipitate is washed with 80 g of isopropanol and the filtrate is freed from low boilers by distillation. The residue is distilled at 15 mbar. At an overhead temperature of 65° C., 194 g of monoisopropyl methanephosphonite are obtained. This corresponds to a yield of 93% of theory.

EXAMPLE 4

800 g (6.84 mol) of dichloromethylphosphine are added dropwise to 1300 g (28.2 mol) of ethanol at 0°–5° C. under a nitrogen atmosphere, with stirring, in the course of two hours. The temperature is then increased to 27°–28° C., and the mixture is then kept at this temperature with slight cooling for two hours. The content of ionic chlorine is then 13%. The mixture is then cooled to 0° C. and 120 g (7.06 mol) of ammonia gas are passed in in the course of one hour. The mixture is then slowly heated to an internal temperature of 90° C. in order to outgas ethyl chloride. The mixture is then cooled and filtered off with suction and the precipitate washed with 500 g of ethanol. After distilling off the low boilers, the residue is distilled at 12 mbar and an overhead temperature of 60° C. 670 g of monoethyl methanephosphonite are obtained. This corresponds to a yield of 91% of theory.

EXAMPLE 5

306 g (1.71 mol) of dichlorophenylphosphine are added dropwise to 325 g (7.07 mol) of ethanol in the course of two hours at 0°–5° C. under a nitrogen atmosphere with stirring. After further stirring for 30 minutes without cooling, the temperature of the batch is 18° C. and the content of ionic chlorine 11.3%. Ammonia gas is then passed in at –5° to 0° C. for about one hour until the batch gives a neutral reaction. The mixture is then further stirred and filtered off with suction and the precipitate washed with 250 ml of ethanol. After distilling off the low boilers, the residue is distilled in a thin-film evaporator at 0.4 mbar and 125°–130° C. 265 g of monoethyl phenylphosphonite are obtained. This corresponds to a yield of 91% of theory.

EXAMPLE 6

50 g (0.345 mol) of dichloroisopropylphosphine are added dropwise to 65.8 g (1.43 mol) of ethanol in the course of one hour at 0°–5° C. under a nitrogen atmosphere with stirring. After removing the cooling bath, the temperature increases in 25 minutes to 30° C., then the mixture is cooled to 25° C. and further stirred for 5 minutes. The content of ionic chlorine is then 11.0%. The mixture is then cooled to 0° C. and 7 g (0.41 mol) of ammonia gas are passed in. The batch is then heated stepwise to 90° C., with ethyl chloride outgassing. After the mixture is cooled, it is filtered off with suction, the precipitate washed with ethanol and the filtrate worked up by distillation. 39 g of monoethyl isopropylphosphonite are obtained (boiling point: 68°–70° C. at 11 mbar). This corresponds to a yield of 83% of theory.

EXAMPLE 7

48 g (0.30 mol) of dichloroisobutylphosphine are added dropwise to 81.2 g (1.77 mol) of ethanol in the course of 90 minutes at 0° C. under a nitrogen atmosphere with stirring. The cold bath is then removed. The temperature is allowed to rise to 26° C. and is maintained at this temperature with cooling until a chlorine value of 8.3% is determined. The mixture is then cooled to 0° C. and ammonia is passed in until the batch gives a weakly alkaline reaction. The mixture is then allowed to come to room temperature and is then heated stepwise to 70° C., with ethyl chloride outgassing. The mixture is then cooled and filtered off with suction and the precipitate washed with ethanol. The filtrate is worked up by distillation. 42 g of monoethyl isobutylphosphonite are obtained (boiling point: 86°–88° C. at 12 mbar). This corresponds to a yield of 93% of theory.

I claim:

1. A process for preparing monoalkyl phosphonites of the formula I

where

R$^1$ is (C$_1$–C$_{16}$)-alkyl, cyclohexyl, cyclopentyl, phenyl, each of which can also be substituted by halogen, (C$_1$–C$_6$)-alkyl, (C$_1$–C$_6$)-alkoxy or dialkylamino groups and R$^2$ is (C$_1$–C$_6$)-alkyl, which comprises reacting dichlorophosphines of the formula (II)

where R$^1$ has the meaning given above, with alcohols of the formula (III)

where R$^2$ has the meaning given above, at a temperature of at least –20° C., the molar ratio of dichlorophosphine/alcohol being 1:3 to 1:20, and then, as soon as the content of the ionic chlorine in the reaction mixture is 50–75% of the theoretical total chlorine content of the reaction mixture, reacting the mixture with ammonia.

2. The process as claimed in claim 1, wherein R$^2$ is (C$_1$–C$_6$)-alkyl.

3. The process as claimed in claim 1, wherein, as dichlorophosphine of the formula (II), use is made of dichloromethylphosphine, dichloroethylphosphine, dichloropropylphosphine, dichlorobutylphosphine, dichlorocyclohexylphosphine, dichlorophenylphosphine, dichloro-4-methoxyphenylphosphine or dichloro-4-dimethylaminophenylphosphine.

4. The process as claimed in claim 1, wherein, as alcohol R$^2$OH, use is made of methanol, ethanol, isopropanol or n-butanol.

5. The process as claimed in claim 1, wherein the ratio of dichlorophosphine:alcohol is 1:4.5 to 1:15.

6. The process as claimed in claim 1, wherein an inert solvent is additionally used.

7. The process as claimed in claim 1, wherein the dichlorophosphine is added to the alcohol at –20° to +30° C.

8. The process as claimed in claim 1, wherein the mixture is reacted with ammonia as soon as the content of ionic chlorine in the reaction mixture is 50–65%.

9. The process as claimed in claim 1, wherein the ammonia is used in an excess of 5 to 20 mol %.

10. The process as claimed in claim 1, wherein $R^2$ is $(C_1-C_4)$-alkyl.

11. The process as claimed in claim 1, wherein as alcohol $R^2OH$, use is made of ethanol.

12. The process as claimed in claim 6, wherein the inert solvent is toluene or chlorobenzene.

13. The process as claimed in claim 1, wherein the dichlorophosphine is added to the alcohol at $-10°$ to $+10°$ C.

14. The process of claim 2, wherein the dichlorophosphine of formula (II) is selected from the group consisting of: dichloromethylphosphine, dichloroethylphosphine, dichloropropylphosphine, dichlorobutylphosphine, dichlorocyclohexylphosphine, dichlorophenylphosphine, dichloro-4-methoxyphenylphosphine and dichloro-4-dimethylaminophenylphosphine.

15. The process as claimed in claim 2, wherein the alcohol $R^2OH$ is selected from the group consisting of: methanol, ethanol, isopropanol and n-butanol.

16. The process as claimed in claim 2, wherein the ratio of dichlorophosphine:alcohol is 1:4.5 to 1:15.

17. The process as claimed in claim 2, wherein an inert solvent selected from the group consisting of toluene and chlorobenzene is additionally used.

18. The process as claimed in claim 3, wherein the alcohol $R^2OH$ is selected from the group consisting of: methanol, ethanol, isopropanol and n-butanol.

19. The process as claimed in claim 3, wherein the ratio of dichlorophosphine:alcohol is 1:4.5 to 1:15.

20. The process as claimed in claim 3, wherein $R^2$ is $(C_1-C_4)$-alkyl, ethanol is used as the alcohol, the ratio of dichlorophosphine:alcohol is 1:4.5 to 1:15, the dichlorophosphine is added to the alcohol at $-10°$ to $+10°$ C., the mixture is reacted with ammonia as soon as the content of ionic chlorine in the reaction mixture is 50–65%, the ammonia is used in an excess of 5 to 20 mol %, and wherein toluene or chlorobenzene are additionally used as an inert solvent.

* * * * *